United States Patent [19]

Darsow et al.

[11] Patent Number: 5,728,883

[45] Date of Patent: Mar. 17, 1998

[54] PROCESS FOR PREPARING A MIXTURE OF CYCLOHEXYLAMINE AND DICYCLOHEXYLAMINE

[75] Inventors: Gerhard Darsow; Wilfried Niemeier, both of Krefeld; Gerd-Michael Petruck, Erkrath, all of Germany

[73] Assignee: Bayer Aktiengesellschaft, Leverkusen, Germany

[21] Appl. No.: 795,924

[22] Filed: Feb. 5, 1997

[30] Foreign Application Priority Data

Feb. 15, 1996 [DE] Germany .................. 196 05 585.7

[51] Int. Cl.[6] .................................................... C07C 209/72
[52] U.S. Cl. ........................................................... 564/450
[58] Field of Search .................................. 564/450, 451, 564/449

[56] References Cited

U.S. PATENT DOCUMENTS

| | | |
|---|---|---|
| 3,636,108 | 1/1972 | Brake . |
| 4,057,513 | 11/1977 | Biedermann et al. . |
| 4,429,155 | 1/1984 | Göetz et al. . |
| 5,322,965 | 6/1994 | Immel et al. . |
| 5,386,060 | 1/1995 | Immel et al. . |

FOREIGN PATENT DOCUMENTS

| | | |
|---|---|---|
| 0053818 | 6/1982 | European Pat. Off. . |
| 0501265 | 9/1992 | European Pat. Off. . |
| 0503347 | 9/1992 | European Pat. Off. . |
| 1530477 | 7/1968 | France . |
| 2300617 | 9/1976 | France . |
| 805518 | 5/1951 | Germany . |
| 765846 | 6/1953 | Germany . |
| 1106319 | 1/1958 | Germany . |
| 1106319 | 5/1961 | Germany . |
| 318068 | 8/1968 | Japan . |
| 969542 | 9/1964 | United Kingdom . |

*Primary Examiner*—Brian M. Burn
*Attorney, Agent, or Firm*—Sprung Kramer Schaefer & Briscoe

[57] ABSTRACT

In the preparation of a mixture of cyclohexylamine and dicyclohexylamine by catalytic hydrogenation of aniline at elevated temperature and elevated $H_2$ pressure, use is made of reduced, support-free catalysts which comprise pressed element (hydr)oxide powders of Co, Mn, alkaline earth metals and element (hydr)oxide powders of elements of transition groups V and/or VI of the Periodic Table.

14 Claims, No Drawings

PROCESS FOR PREPARING A MIXTURE OF CYCLOHEXYLAMINE AND DICYCLOHEXYLAMINE

BACKGROUND OF THE INVENTION

1. Field of the Invention

The invention relates to a continuous process for preparing a mixture of unsubstituted or substituted cyclohexylamine and unsubstituted or substituted dicyclohexylamine in variable amounts by catalytic hydrogenation of unsubstituted or substituted aniline with hydrogen at elevated temperature and elevated pressure using fixed-bed catalysts obtained by reduction of shaped bodies comprising pressed powders of cobalt, manganese and alkaline earth metal (hydr)oxides and (hydr)oxides of elements of transition groups V and/or VI of the Periodic Table of the Elements (Mendeleev). Unsubstituted or substituted cyclohexylamines and dicyclohexylamines are used for producing ageing inhibitors for rubbers and plastics, as corrosion inhibitors in aqueous solution, and also as precursors for textile assistants and crop protection agents.

2. Description of the Related Art

It is known that cyclohexylamine can be prepared by pressure hydrogenation of aniline. This hydrogenation is carried out in using mainly expensive noble metal catalysts, for example, according to U.S. Pat. No. 3,636,108, an Ru catalyst moderated with alkali metal; additional use of $NH_3$ and, if desired, a solvent is made here. A further process for the pressure hydrogenation of aniline to give cyclohexylamine is described in DE-B 1 106 319, where an Ru catalyst is likewise used. In this process, dicyclohexylamine which is also formed is added back to the starting material. However, owing to the simultaneous formation of cyclohexane, this process achieves only a moderate yield. According to EP-B 53 818, supported Pd catalysts are better than Ru catalysts; the catalysts described therein contain additives which originate either from a group of basic compounds of the alkali metals, alkaline earth metals and rare earth metals or a group which comprises the metal Fe, Ni, Co, Mn, Zn, Cd and Ag. These catalysts allow the reduction of substituted anilines to give the corresponding cyclohexylamines, but the corresponding dicyclohexylamines are completely absent. This applies similarly to Co catalysts which contain a basic additive (GB 969 542) and also to Raney Co (JP 68/03 180).

In the pressure hydrogenation processes of aniline described, the dicyclohexylamine is formed only as by-product to the cyclohexylamine, or not at all. To obtain dicyclohexylamine in larger amounts, it is prepared by separate processes. Thus, for example, it can be obtained by pressure hydrogenation of diphenylamine using an $Ru/Al_2O_3$ catalyst (DE-B 1 106 319 above). Dicyclohexylamine is also formed in the reaction of cyclohexanone with cyclohexylamine in the presence of Pd on carbon under a hydrogen pressure of 4 bar (FR 1 530 477).

In a cumbersome process, dicyclohexylamine can be obtained from the hydrogenation product of aniline over an Ni catalyst by fractional condensation. From the remaining mixture, part of the ammonia also formed is removed and the remainder is returned to the reaction (DE-C 805 518).

A problem common to all these processes for the ting hydrogenation of aromatic amines is the sometimes considerable formation of cyclohexane as a by-product which cannot be further used. There was therefore a continuing desire to develop a new process which can also be used on an industrial scale and makes it possible to prepare both cyclohexylamine and dicyclohexylamine in a desired ratio, in which process the loss resulting from the undesired formation of cyclohexane is suppressed and, furthermore, the life of the catalyst used is improved.

EP-A 501 265 discloses a process for preparing unsubstituted or substituted cyclohexylamine and unsubstituted or substituted dicyclohexylamine by catalytic hydrogenation of unsubstituted or substituted aniline, using a catalyst comprising Ru, Pd or a mixture of both metals applied to a support of niobic acid or tantalic acid or to a mixture of the two. EP-A 503 347 discloses a further process for preparing unsubstituted or substituted cyclohexylamine and unsubstituted or substituted dicyclohexylamine by hydrogenation of a correspondingly substituted aniline, using a catalyst where an α- or γ-$Al_2O_3$ as support is first treated with at least one compound of rare earth metals and with at least one compound of manganese and then with at least one Pd compound. The preparation of the catalysts in these processes of EP-A 501 265 and EP-A 503 347 is technically complicated and their use is expensive since the recovery of the noble metal content from the complex mixtures of substances after the catalyst is exhausted creates considerable problems which were not recognized at the beginning. In addition, in this process the ratio of the cyclic amines which can be prepared is shifted too much in the direction of higher proportions of dicyclohexylamine. Finally, the life of the catalysts used in the last-named processes is, at from 3000 to 4000 hours, too short, so that they have not been able to achieve what was expected of them.

Surprisingly, it has now been found that the abovementioned requirements can be fulfilled by the use of inexpensive oxidic fixed-bed catalysts which are free of inactive support material and can therefore be worked up and disposed of simply.

SUMMARY OF THE INVENTION

The invention accordingly provides a process for preparing a mixture of cyclohexylamine and dicyclohexylamine of the formulae;

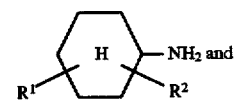  (I)

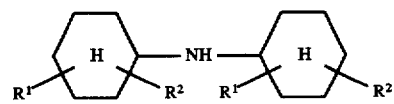  (II)

by catalytic hydrogenation of aniline of the formula

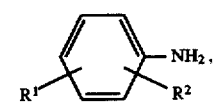  (III)

where, in the formulae, $R^1$ and $R^2$ are, independently of one another, hydrogen, $C_1-C_4$-alkyl or $C_1-C_4$-alkoxy, at a reaction temperature of from 140° to 240° C. and an $H_2$ pressure of from 10 to 400 bar, wherein the catalysts used are support-free solid bodies comprising pressed powders of cobalt, manganese and alkaline earth metal (hydr)oxides and of (hydr)oxides of at least one element of transition groups V and/or VI of the Periodic Table of the Elements (Mendeleev).

DETAILED DESCRIPTION OF THE INVENTION

For the catalysts to be used according to the invention, the Co contents (in each case calculated as metal) are from 40 to 65% by weight, the Mn contents are from 10 to 20% by weight, the alkaline earth metal contents are from 0.2 to 5% by weight and the contents of elements of transition groups V and/or VI of the Periodic Table are a total of from 0.5 to 5% by weight. The remainder to 100% by weight is oxygen for the compounds present in oxidic form. Cu can be present in an amount of 0–3% by weight.

Suitable alkaline earth metal elements are especially magnesium, calcium, strontium and barium, preferably strontium and barium. Suitable elements of transition group V are preferably vanadium, niobium and tantalum, suitable elements of transition group VI are preferably chromium, molybdenum and tungsten. The elements of transition groups V and VI, which act as promoters, can be used either individually or as a mixture of a plurality of these elements.

The catalysts are prepared using powders of oxides or hydroxides of the elements mentioned. Preference is given to using oxide powders of the elements mentioned. Such powders are mechanically mixed with one another in such amounts that they fulfill the abovementioned weight ratios. The remainder to 100% by weight is ways the oxygen content, and all percentages by weight are based on the total weight of the oxidic, support-free shaped body. The mixture of the powders is then pressed under high pressure on tableting or pelletizing machines, with use also being able to be made of graphite, adhesives or both in amounts of 0.5–1% by weight, based on the total weight of the powders to be pressed, for improving the adhesion of the powders. Examples of the shape of such compacts are pellets, spheres or cylindrical granules having dimensions of 1–10 mm, preferably 3–7 mm. Tableted bodies can be further provided with an axial hole to increase the external surface area. Viewed macroscopically, such pressed bodies have a smooth surface. The pressed shaped bodies have a high compressive strength on the surface of the body. Thus, pellets or cylindrical granules have a compressive strength on the flat surfaces of 200–800N/cm$^2$, preferably 250–600N/cm$^2$, when using a flat ram, and pellets, spheres or cylindrical granules have a compressive strength on the curved surfaces of 50–200N (measured as force), preferably 80–140N, when using a knife-indenter. The internal surface area of the pressed shaped bodies used is 30–200 m$^2$/g, preferably 80–160 m$^2$/g. The compressive strength of the support-free shaped bodies can be determined in accordance with DIN 50 106. The internal surface area is determined using the method of F. M. Nelsen and F. T. Eggertsen, Analyt. Chem. 30, (1958), pp. 1387–1390 or using the method of S. J. Gregg and K. S. W. Sing, Adsorption Surface Area and Porosity, Academic Press, London 1982, chapters 2 and 6.

Using the catalysts described, the process of the invention produces a mixture of unsubstituted or substituted cyclohexylamine and unsubstituted or substituted dicyclohexylamine. Surprisingly, the ratio of the two amines can be altered as a function of the hydrogenation temperature: increasing the temperature gives more unsubstituted or substituted dicyclohexylamine and less unsubstituted or substituted cyclohexylamine, and reducing the temperature has the opposite effect.

The temperature range for the process of the invention is 140°–240° C., preferably 160°–230° C. It is carried out at an H$_2$ pressure of 10–400 bar, preferably 20–350 bar, particularly preferably 100–300 bar.

The process of the invention can, using the catalysts arranged in a fixed bed, be carried out continuously in the gas phase or in a trickling phase, with at least 10 times the molar amount of hydrogen per mole of starting material passing through the reactor during the course of the process. Preference is given to carrying out the process in a trickling phase. The hydrogenation reactors can be individual high-pressure tubes of steel or a steel alloy which are completely or partly filled with the shaped bodies; in case of relatively large tube cross sections, the use of the support-free shaped bodies on trays such as wire baskets or similar internal fittings can also be beneficial. It is also possible to employ high-pressure tube bundles within a common jacket, with the individual tubes again being filled completely or partly with the shaped catalyst bodies.

The pressed, support-free catalysts are reduced by hydrogen and thus activated. This is in principle possible simultaneously with the hydrogenation of the starting material used, but here a longer running-in phase is required before the catalysts reach their full activity and thus the highest possible space-time yield is obtained. It is therefore advantageous to reduce the catalyst before passing the starting material through it. This activating reduction with hydrogen is carried out in the temperature range of 160°–240° C. and in the pressure range of 10–400 bar. Here, the atmospheric oxygen initially present is firstly completely removed by means of an inert gas such as nitrogen, argon, methane or ethane before an amount of 10–15% by volume of hydrogen is added to the inert gas. The inert gas is preferably nitrogen because of the ready availability of the latter. Over a fixed period of time, for example 24 hours, the proportion of inert gas is then continually reduced and finally the inert gas is completely removed so that activation and reduction are carried out using pure hydrogen. The reduction is complete when the catalyst no longer consumes any hydrogen and as a result thereof no longer forms any water of reaction.

For the process carried out in a trickling phase, the weight hourly space velocity is 0.1–3 kg, preferably 0.15–1.5 kg, of unsubstituted or substituted aniline per liter of catalyst and hour. The unsubstituted or substituted aniline used can be diluted with a suitable reaction-inert solvent, for example with cyclohexane or cyclohexanol in an amount of 10–100% by weight, preferably 10–40% by weight, based on the weight of the unsubstituted or substituted aniline. The addition of cyclohexanol in the amount indicated, which can be replaced completely or partly by cyclohexanone or phenol, also makes it possible to trap by amination the ammonia liberated in the process and to form further unsubstituted or substituted cyclohexylamine/dicyclohexylamine. In the continuous procedure in a trickling phase it can be useful to hydrogenate the unsubstituted or substituted aniline incompletely, and instead aim for a conversion of 80–97%.

The catalysts used according to the invention have very long operating lives; up to now from 12,000 to 15,000 hours have been observed, with the corresponding experiments having been stopped without a noticeable fall in the activity. These operating lives are multiples of those described in the abovementioned EP-A 501 265 and EP-A 503 347.

Suitable starting materials for the process of the invention are unsubstituted or substituted anilines of the above formula (III). C$_1$–C$_4$-Alkyl and C$_1$–C$_4$-alkoxy substituents which may be present are, for example, methyl, ethyl, propyl, isopropyl, butyl, isobutyl, methoxy, ethoxy, propoxy, isopropoxy, butoxy, isobutoxy. Of these, preference is given to methyl, ethyl, methoxy and ethoxy as possible substituents. The substituents are particularly preferably methyl or methoxy. Furthermore, R$^2$ is preferably hydrogen, while R$^1$ can assume the meanings given above. Very particular preference is given to hydrogenating unsubstituted aniline to give unsubstituted cyclohexylamine and unsubstituted dicyclohexylamine.

The reaction mixtures obtained after the hydrogenation contain no cyclohexane unless this has been added as solvent, so that particularly high contents of unsubstituted or substituted cyclohexylamine and unsubstituted or substituted dicyclohexylamine can be achieved. The hydrogenation mixtures can be worked up by simple distillation. For such a work-up, it can be advantageous to react the unsubstituted or substituted aniline incompletely. The incompletely reacted aniline can be returned to the reaction. The unconsumed par of the hydrogen added in a 10–80-fold molar excess can also be returned to the reaction. Advantageously, the major part of this unreacted hydrogen is recovered in a high-pressure separator so that the work of compression for the hydrogen does not have to be expended again.

The unsubstituted or substituted cyclohexylamine and the unsubstituted or substituted dicyclohexylamine prepared according to the invention are obtained in a purity of at least 99.9% by weight after separation by distillation. In this purity, said compounds are generally usable for all further processes.

The ability to vary the process of the invention is shown by a strong increase in the proportion of unsubstituted or substituted dicyclohexylamine compared with the unsubstituted or substituted cyclohexylamine with rising temperature under otherwise identical conditions. Thus, for example, the proportion of unsubstituted or substituted dicyclohexylamine formed in the temperature range of about 180°–230° C. is 2–10 times the proportion in the temperature range of 170°–175° C.

EXAMPLES

Example 1

An upright, heat-insulated high-pressure tube of stainless, acid-resistant steel having an internal diameter of 90 mm and a length of 1.8 mm, which had previously been flushed oxygen-free using nitrogen, was charged with 11.4 l of a hydrogenation catalyst prepared by tableting powders of cobalt, manganese, barium and molybdenum oxides. The Co content of the pellets was 53% by weight, the Mn content was 14% by weight, the Ba content was 1.1% by weight and the Mo content was 1.2% by weight (remainder to 100%: oxygen). The pellets had a cylinder height of 5 mm, a diameter of 5 mm and a compressive strength of 420N/cm² on the cross-sectional surface and of 125N, measured as force, on the cylindrical surface, and also an internal surface area of 168 m²/g.

The pellets are first dried for 6 hours in a stream of nitrogen (temperature: max. 200° C., amount: 5 standard m³ of N₂/h). The activation was then carried out under a nitrogen pressure of 200 bar at a temperature between 180° and 240° C., with hydrogen gradually being mixed into the nitrogen in an amount of initially from 10 to 15% by volume. Over a period of 24 hours, the proportion of nitrogen in the gas mixture was steadily decreased until finally pure hydrogen flowed through the reactor. The activation was complete as soon as water of reaction no longer collected in the downstream separator. After activation of the catalyst, the hydrogen pressure in the reactor system was increased to 300 bar. Subsequently, 2280 g/h of aniline was pumped in the trickling mode through the high-pressure tube together with 70 standard m³/h of hydrogen under a pressure of 300 bar, with the aniline to be hydrogenated being heated to a temperature of 160° C. in an upstream electrically heated heat exchanger before entering the first high-pressure tube.

The reaction product leaving the reaction tube was cooled to a temperature of <60° C. in a second heat exchanger (water cooler) under 300 bar of hydrogen pressure and separated in a gas separator from the excess hydrogen which could be returned to the hydrogenation system. After further cooling to a temperature of <30° C. and depressurization to atmospheric pressure, the reaction product was analyzed by gas chromatography. Under steady-state reaction conditions, the following product composition was obtained as a function of the reaction temperatures (given in % by area (A-%), CHA=cyclohexylamine, DCHA=dicyclohexylamine, the remainder to 100% is aniline and by-products; individual running times at the respective temperatures):

| Running time (h) | Temperature (°C.) | CHA (A-%) | DCHA (A-%) |
|---|---|---|---|
| 500 | 175 | 86.8 | 3.7 |
| 452 | 180 | 89.3 | 7.5 |
| 404 | 185 | 86.5 | 12.7 |
| 116 | 190 | 77.3 | 21.8 |
| 212 | 200 | 71.6 | 27.0 |
| 236 | 210 | 62.9 | 34.1 |
| 308 | 220 | 54.8 | 38.5 |
| 380 | 230 | 46.9 | 40,3 |

Example 2

A high-pressure tube as in Example 1, which had previously been flushed oxygen-free using nitrogen, was charged with 11.4 l of a hydrogenation catalyst prepared by tableting powders of cobalt, manganese, copper, barium and vanadium oxides. The Co content of the pellets was 52% by weight, the Mn content was 16% by weight, the Cu content was 0.18% by weight, the Ba content was 0.91% by weight and the V content was 1.1% by weight (remainder to 100%: oxygen). The pellets had a cylinder height of 7 mm, a diameter of 7 mm and a compressive strength of 420N/cm² on the cross-sectional surface and of 160N on the cylindrical surface, and also an internal surface area of 180 m²/g. The pellets were dried and activated as in Example 1. After activation of the catalyst, the hydrogen pressure in the reactor system was increased to 300 bar. Subsequently, 2280 g/h of aniline were pumped in the trickling mode through the high-pressure tube together with 70 standard m³/h of hydrogen under a pressure of 300 bar, with the aniline to be hydrogenated being heated to a temperature of 160° C. in an upstream electrically heated heat exchanger before entering the first high-pressure tube. The reaction product leaving the reaction tube was cooled to a temperature of <60° C. in a second heat exchanger (water cooler) under 300 bar of hydrogen pressure and separated in a gas separator from the excess hydrogen which was returned to the hydrogenation system. After further cooling to a temperature of <30° C. and depressurization to atmospheric pressure, the reaction product was analyzed by gas chromatography. Under steady-state reaction conditions, the following product composition was obtained as a function of the reaction temperatures (definitions as in Example 1; individual running times at the respective temperatures):

| Running time (h) | Temperature (°C.) | CHA (A-%) | DCHA (A-%) |
|---|---|---|---|
| 525 | 190 | 92.8 | 5.00 |
| 94 | 200 | 89.2 | 10.20 |
| 142 | 210 | 80.5 | 17.95 |
| 166 | 220 | 78.8 | 18.00 |

-continued

| Running time (h) | Temperature (°C.) | CHA (A-%) | DCHA (A-%) |
| --- | --- | --- | --- |
| 223 | 230 | 69.1 | 24.30 |
| 240 | 240 | 55.8 | 28.40 |

Example 3

An upright, heat-insulated high-pressure tube of stainless, acid-resistant steel having an internal diameter of 45 mm and a length of 1 m, which had previously been flushed oxygen-free using nitrogen, was charged with 1.4 l of a shaped body produced by tableting powders of cobalt, manganese, copper, strontium and tungsten oxides. The Co content of the pellets was 53% by weight, the Mn content was 14% by weight, the Cu content was 0.2% by weight, the Sr content was 0.9% by weight and the W content was 1.1% by weight (remainder to 100%: oxygen). The pellets had a cylinder height of 6 mm, a diameter of 6 mm and a compressive strength of 533N/cm$^2$ on the cross-sectional surface and of 162N on the cylindrical surface, and also an internal surface area of 142 m$^2$/g.

The pellets were dried and activated as in Example 1. After activation of the hydrogenation catalyst, the hydrogen pressure in the reactor system was increased to 300 bar. Subsequently, 560 g/h of aniline were pumped downward in the trickling mode through the high-pressure tube together with 10 standard m$^3$/h of hydrogen under a pressure of 300 bar, with the aniline being heated to a temperature of 160° C. in an upstream electrically heated heat exchanger before entering the reactor. The reaction product leaving the reaction tube was cooled to a temperature of <60° C. in a second heat exchanger (water cooler) under 300 bar of hydrogen pressure and separated in a gas separator from the excess hydrogen which could be returned to the hydrogenation system. After further cooling to a temperature of <30° C. and depressurization to atmospheric pressure, the reaction product was analyzed by gas chromatography. Under steady-state reaction conditions, the following product composition was obtained as a function of the reaction temperatures (definitions as in Example 1; cumulative running times).

| Running time (h) | Temperature (°C.) | CHA (A-%) | DCHA (A-%) |
| --- | --- | --- | --- |
| 64 | 180 | 84.2 | 8.5 |
| 118 | 190 | 78.6 | 19.7 |
| 542 | 200 | 74.1 | 29.4 |
| 812 | 210 | 68.6 | 31.1 |
| 1112 | 220 | 64.1 | 35.2 |
| 1422 | 230 | 54.1 | 43.8 |

Example 4

A high-pressure tube as in Example 1 was charged with 11.4 l of a hydrogenation catalyst prepared by tableting powders of cobalt, manganese, copper, barium and molybdenum oxides. The Co content of the pellets was 53% by weight, the Mn content was 14% by weight, the Cu content was 0.2% by weight, the Ba content was 0.9% by weight and the Mo content was 1.1% by weight. The pellets had a cylinder height of 6 mm, a diameter of 6 mm and a compressive strength of 425N/cm$^2$ on the cross-sectional surface and of 160N on the cylindrical surface, and also an internal surface area of 180 m$^2$/g. The oxidic hydrogenation catalyst was dried and activated as in Example 1, and the hydrogen pressure was increased to 300 bar. Subsequently, 2280 g/h of aniline were pumped in the trickling mode through the high-pressure tube together with 70 standard m$^3$/h of hydrogen under a pressure of 300 bar, with the aniline to be hydrogenated being heated to a temperature of 200° C. in an upstream electrically heated heat exchanger before entering the high-pressure tube. The reaction product leaving the reaction tube was cooled to a temperature of <60° C. in a second heat exchanger (water cooler) under 300 bar of hydrogen pressure and separated in a gas separator from the excess hydrogen which was returned to the hydrogenation system. After further cooling to a temperature of <30° C. and depressurization to atmospheric pressure, the reaction product was analyzed by gas chromatography. Under steady-state reaction conditions, the following product composition was obtained (definitions as in Example 1; cumulative running times).

| Running time (h) | Temperature (°C.) | CHA (A-%) | DCHA (A-%) |
| --- | --- | --- | --- |
| 182 | 199 | 71.6 | 27.0 |
| 2,978 | 198 | 32.9 | 28.4 |
| 5,412 | 205 | 66.8 | 32.8 |
| 8,216 | 208 | 62.6 | 35.8 |
| 14,458 | 210 | 62.8 | 36.2 |

What is claimed is:

1. A process for preparing a mixture of a cyclohexylamine and a dicyclohexylamine of the formulae

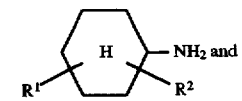 (I)

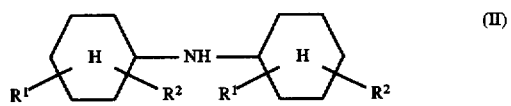 (II)

by catalytic hydrogenation of an aniline of the formula

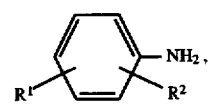 (III)

where, in the formulae, $R^1$ and $R^2$ are, independently of one another, hydrogen, $C_1$-$C_4$-alkyl or $C_1$-$C_4$-alkoxy, at a reaction temperature of from 140° to 240° C. and an $H_2$ pressure of from 10 to 400 bar, wherein the catalyst used comprises support-free shaped bodies which are obtainable by reduction of shaped bodies comprising pressed powders of cobalt, manganese and alkaline earth metal (hydr)oxides and of (hydr)oxides of elements of transition groups V, VI or both of the Periodic Table of the Elements (Mendeleev).

2. The process of claim 1, wherein the shaped bodies of pressed metal oxide powders to be used for the reduction contain from 40 to 65% by weight of cobalt, from 10 to 20% by weight of manganese, from 0.2 to 5% by weight of alkaline earth metal and from 0.2 to 5% by weight of elements of transition groups V, VI or both of the Periodic Table (in each case calculated as metals), where the percentages are based on the total amount of metal oxide powder mixture and the remainder to 100% by weight is oxygen.

3. The process of claim 1, wherein the catalyst has a compressive strength of 200–800N/cm$^2$ on flat surfaces, a compressive strength of 50–200N, measured as force, on curved surfaces and an internal surface area of 30–200 m$^2$/g.

4. The process of claim 3, wherein the catalyst has a compressive strength of 250–600 N/cm² on flat surfaces.

5. The process of claim 3, wherein the catalyst has a compressive strength of 80–100N, measured as force, on curved surfaces.

6. The process of claim 3, wherein the catalyst has an internal surface area of 80–160 m²/g.

7. The process of claim 1, wherein the reaction is carried out continuously in the trickling phase over fixed-bed catalysts and the weight hourly space velocity used is 0.1–3 kg of aniline per liter of catalyst and hour.

8. The process of claim 7, wherein the weight hourly space velocity is 0.15–1.5 kg.

9. The process of claim 1, wherein the reaction is carried out at an $H_2$ pressure of 20–350 bar.

10. The process of claim 9, wherein the reaction is carried out at an $H_2$ pressure of 100–300 bar.

11. The process of claim 1, wherein the reaction is carried out at a temperature of 160°–230° C.

12. The process of claim 1, wherein the catalyst is reduced before use by treatment with hydrogen at 160°–240° C. and 10–400 bar, with the hydrogen being used as an $H_2$/inert gas mixture at the beginning of the reduction and the inert gas component being completely removed during the course of the reduction.

13. The process of claim 1, wherein the unsubstituted or substituted aniline is diluted with 10–100% by weight of a reaction-inert solvent, based on the unsubstituted or substituted aniline.

14. The process of claim 13, wherein the reaction-inert solvent is of 10–40% by weight, based on the unsubstituted or substitute aniline.

* * * * *